(12) United States Patent
Arai et al.

(10) Patent No.: US 11,712,255 B2
(45) Date of Patent: Aug. 1, 2023

(54) SURGICAL DRILL GUIDES AND SYSTEMS

(71) Applicant: Smith & Nephew, Inc., Memphis, TN (US)

(72) Inventors: Tatsuya Arai, Memphis, TN (US); Matthew Edwin Koski, Memphis, TN (US); Timothy Young, Memphis, TN (US); Nehal Navinbhai Patel, Memphis, TN (US); Geoffrey Ian Karasic, Memphis, TN (US); Marc Joseph Balboa, Memphis, TN (US)

(73) Assignee: SMITH & NEPHEW, INC., Memphis, TN (US)

( * ) Notice: Subject to any disclaimer, the term of this patent is extended or adjusted under 35 U.S.C. 154(b) by 257 days.

(21) Appl. No.: 17/377,814

(22) Filed: Jul. 16, 2021

(65) Prior Publication Data

US 2021/0338254 A1  Nov. 4, 2021

Related U.S. Application Data

(63) Continuation of application No. 16/617,210, filed as application No. PCT/US2018/039009 on Jun. 22, 2018, now Pat. No. 11,096,700.

(60) Provisional application No. 62/523,451, filed on Jun. 22, 2017.

(51) Int. Cl.
*A61B 17/17* (2006.01)
*A61B 17/16* (2006.01)

(52) U.S. Cl.
CPC ...... *A61B 17/1796* (2013.01); *A61B 17/1631* (2013.01); *A61B 17/1633* (2013.01); *A61B 17/17* (2013.01)

(58) Field of Classification Search
CPC .. A61B 17/1796; A61B 17/1631; A61B 17/17
See application file for complete search history.

(56) References Cited

U.S. PATENT DOCUMENTS

| | | | | |
|---|---|---|---|---|
| 5,520,693 A | * | 5/1996 | McGuire | B25G 3/26 606/88 |
| 6,197,031 B1 | * | 3/2001 | Barrette | A61B 17/164 606/311 |
| 10,022,131 B1 | * | 7/2018 | Burley | A61B 17/1631 |
| 2008/0188854 A1 | * | 8/2008 | Moser | A61B 17/1631 606/80 |

(Continued)

FOREIGN PATENT DOCUMENTS

WO    WO-2012048050 A1 *  4/2012 ......... A61B 17/0401

OTHER PUBLICATIONS

Japanese Application No. 2019-566078 Notice of Reasons for Rejection dated May 27, 2022.

(Continued)

*Primary Examiner* — Christian A Sevilla
(74) *Attorney, Agent, or Firm* — Burns & Levinson, LLP; Joseph M. Maraia

(57) ABSTRACT

Surgical drill guides having a guide shaft and a set of distal guide teeth extending from the guide shaft. The guide shaft has proximal and distal portions having two distinct inner and outer diameters, with a tapered zone extending between the two portions. Wall thickness is maintained or increased from the proximal portion to the distal portion of the shaft, reinforcing the rigidity of both the shaft and the distal guide teeth.

8 Claims, 9 Drawing Sheets

(56) References Cited

U.S. PATENT DOCUMENTS

| | | | |
|---|---|---|---|
| 2011/0015674 A1* | 1/2011 | Howard | A61B 17/0469 606/232 |
| 2013/0296864 A1* | 11/2013 | Burley | A61B 17/17 606/80 |
| 2014/0107657 A1* | 4/2014 | Norton | A61B 17/0401 606/232 |

OTHER PUBLICATIONS

Chinese Application No. 201880035716.1 The First Office Action and Search Report dated Aug. 2, 2022.

* cited by examiner

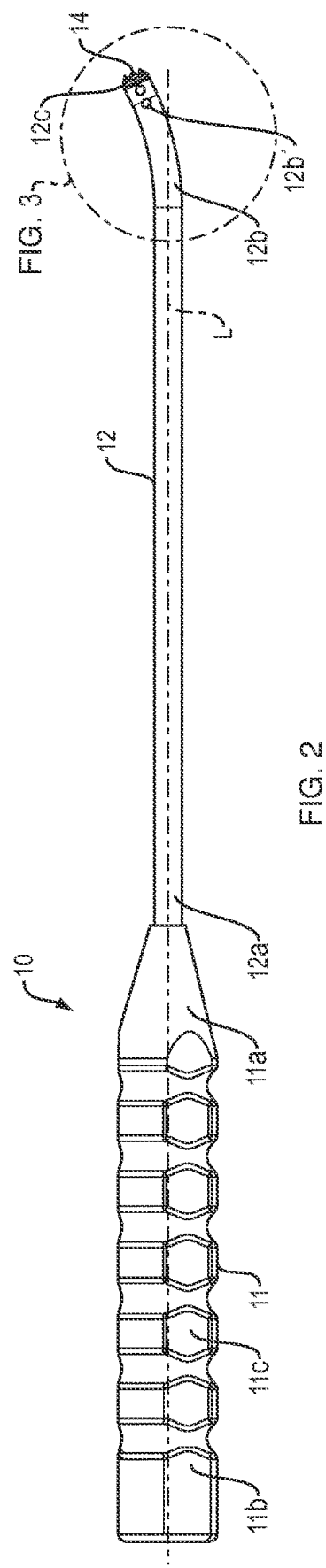
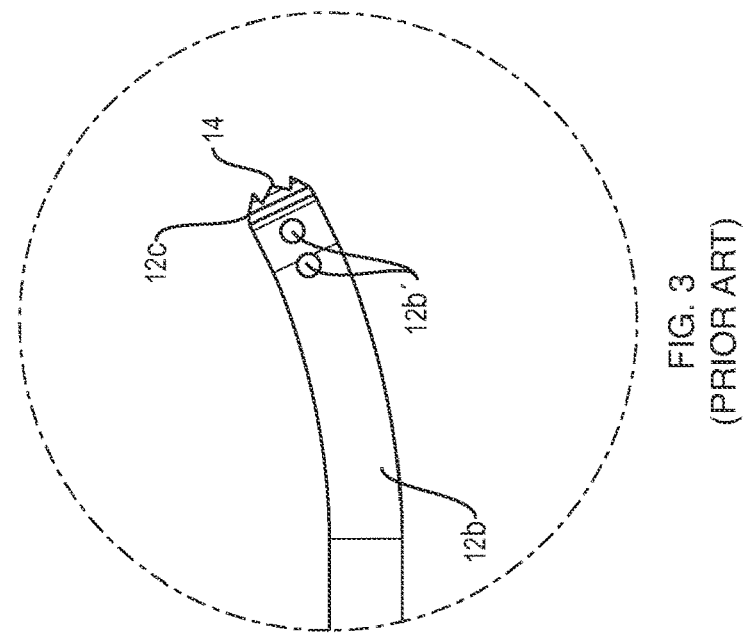
FIG. 2
(PRIOR ART)
FIG. 3
(PRIOR ART)

ically accurate repair. Moreover, in curved guides, a larger inner diameter is also maintained in the bent region of the curve, allowing for a smaller and more distal (relative to the handle) bend radius and a larger bend angle of the guide, which is favorable for accessing constricted areas.

SURGICAL DRILL GUIDES AND SYSTEMS

CROSS-REFERENCE TO RELATED APPLICATIONS

This application is a continuation of co-pending U.S. application Ser. No. 16/617,210, which in turn is the U.S. national phase entry under 35 U.S.C. § 371 of International Application No. PCT/US2018/039009, filed Jun. 22, 2018, entitled SURGICAL DRILL GUIDES AND SYSTEMS, which in turn claims priority to and benefit of U.S. Provisional Application No. 62/523,451, filed Jun. 22, 2017, the contents of which are incorporated herein by reference in their entirety for all purposes.

FIELD

This disclosure relates to surgical drill guides and, more particularly, to flexible drill guide systems for soft tissue repair.

BACKGROUND

Arthroscopic procedures using sutures and suture anchors have been used in surgical repairs to, for example, secure soft tissue to bone. A suture anchor delivery system is generally composed of an inserter device with an attached anchor, a drill for bone tunnel preparation, and a guide for introducing the drill into the repair site. The inserter and the soft tissue anchor can also be introduced into the repair location by means of the drill guide.

In current drill guide design, there are a number of competing features that are important for establishing the position and trajectory of the passing instruments to the repair site. For example, some repairs require anchors to be placed as close to an anatomic margin as possible. In these cases, guides having smaller distal outer diameters are desirable, since this allows the center point of the guide shaft to be closer to the anatomical margin. However, narrowing the diameter at the distal end of the guide generally results in sacrificing wall thickness and rigidity of the distal teeth which allow for secure placement of the guide onto the bone. In curved guides, moreover, a larger inner diameter is desirable in the bent region to allow more room for the rigid portions of the passing instruments to navigate through. However, it is also desirable for the inner diameter at the distal end of the guide to be smaller in order to tightly constrain the exit trajectory of the passing instruments, reducing the risk of iatrogenic damage. Some current guides accommodate a smaller inner diameter at the distal end by having a larger radius of curvature and a smaller angle in the bent area of the guide. However, this configuration is less desirable for accessing hard-to-reach or hard-to-visualize anatomical areas.

BRIEF SUMMARY

Described herein is a surgical drill guide having a guide shaft and a set of distal guide teeth extending from the guide shaft. The guide shaft has proximal and distal portions having two distinct inner and outer diameters, with a tapered zone extending between the two portions. In the drill guide of this disclosure, wall thickness is maintained or increased from the proximal portion to the distal portion of the shaft, reinforcing the rigidity of both the shaft and the distal guide teeth. A smaller inner diameter in the distal portion of the shaft facilitates a predictable and accurate exit trajectory of passing instruments, allowing for a more anatomically accurate repair. Moreover, in curved guides, a larger inner diameter is also maintained in the bent region of the curve, allowing for a smaller and more distal (relative to the handle) bend radius and a larger bend angle of the guide, which is favorable for accessing constricted areas.

Further examples of the surgical drill guide of this disclosure may include one or more of the following, in any suitable combination.

In examples, the surgical drill guide of this disclosures includes a shaft having a proximal portion and a distal portion. The distal portion includes a tapered portion and a distal end. An outer diameter of the proximal portion is selected to be larger than an outer diameter of the distal end. The proximal portion and the distal end separated by the tapered portion. The guide also includes a bore defined by a wall of the shaft extending from a proximal end to the distal end of the shaft. The wall defining a plurality of teeth extending from the distal end. A thickness of the wall of the distal end is selected to be the same as or greater than a thickness of the wall of the proximal portion.

In further examples, the guide includes a handle coupled to the proximal end of the shaft. The shaft is made of a metal material. The distal portion of the shaft is angled relative to a longitudinal axis of the proximal portion. In examples of the angled shaft, the wall defines a flat section at a highest point of a bend in the distal portion and/or at least one of the plurality of teeth is modified or removed to facilitate passage of the guide through a cannula. The distal portion includes at least one transverse hole in communication with the bore. In examples, the tapered portion is formed in one piece or in multiple pieces. A projected plane across points of the plurality of teeth is angled with respect to an outer diameter of the distal end of the guide. An inner diameter of the distal portion is selected to be smaller than an inner diameter of the proximal portion.

Examples of a surgical drill guide system of this disclosure include a drill guide having a shaft with a proximal portion and a distal portion. The distal portion includes a tapered portion and a distal end. An outer diameter of the proximal portion is selected to be larger than an outer diameter of the distal end. The proximal portion and the distal end are separated by the tapered portion. The guide also includes a bore defined by a wall of the shaft extending from a proximal end to the distal end of the shaft, the wall defining a plurality of teeth extending from the distal end. A thickness of the wall of the distal end is selected to be the same as or greater than a thickness of the wall of the proximal portion. The system also includes a flexible drill extending through the bore from the proximal end to the distal end of the shaft.

In further examples, the drill is made of Nitinol. An As temperature of the Nitinol is selected to be greater than an operating temperature of the drill. At least a portion of the Nitinol is in a martensitic state and the Nitinol is machined while in a superelastic state. The drill further includes a sheath which extends through the bore from the proximal end to a region proximal to the distal portion of the shaft. The sheath is made of a material selected to be more rigid than a material of the drill. The shaft is made of a metal material. The distal portion of the shaft is angled relative to a longitudinal axis of the proximal portion of the shaft. The distal portion includes at least one transverse hole in communication with the bore. In examples, the tapered portion is formed in one piece or in multiple pieces.

These and other features and advantages will be apparent from a reading of the following detailed description and a review of the associated drawings. It is to be understood that both the foregoing general description and the following detailed description are explanatory only and are not restrictive of aspects as claimed.

BRIEF DESCRIPTION OF THE DRAWINGS

The disclosure will be more fully understood by reference to the detailed description, in conjunction with the following figures, wherein:

FIGS. 1-3 illustrate a prior art curved surgical drill guide;

DETAILED DESCRIPTION

Figure 1:
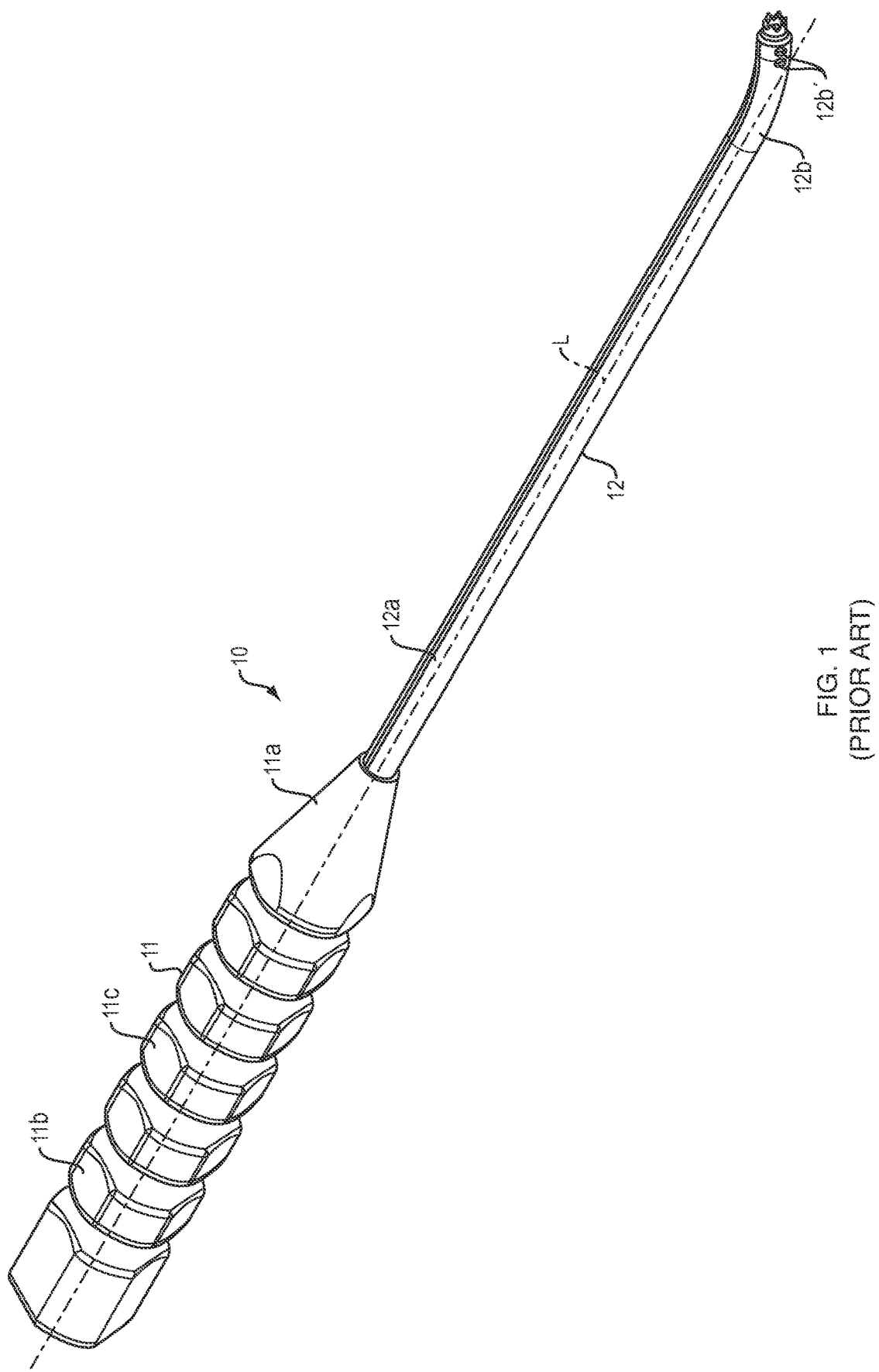

In the description that follows, like components have been given the same reference numerals, regardless of whether they are shown in different examples. To illustrate example (s) in a clear and concise manner, the drawings may not necessarily be to scale and certain features may be shown in somewhat schematic form. Features that are described and/or illustrated with respect to one example may be used in the same way or in a similar way in one or more other examples and/or in combination with or instead of the features of the other examples.

As used in the specification and claims, for the purposes of describing and defining the invention, the terms "about" and "substantially" are used to represent the inherent degree of uncertainty that may be attributed to any quantitative comparison, value, measurement, or other representation. The terms "about" and "substantially" are also used herein to represent the degree by which a quantitative representation may vary from a stated reference without resulting in a change in the basic function of the subject matter at issue. "Comprise," "include," and/or plural forms of each are open ended and include the listed parts and can include additional parts that are not listed. "And/or" is open-ended and includes one or more of the listed parts and combinations of the listed parts.

Turning now to FIG. 1, an exemplary prior art surgical drill guide 10 is shown. The drill guide 10 generally includes a handle 11 and a shaft 12 coupled to the handle 11. In the example shown in FIG. 1, the handle 11 is a cannulated handle 11 having a distal portion 11a, a proximal portion 11b, and an outer surface 11c. However, other configurations of handles 11 are contemplated by this disclosure. For the purposes of this disclosure, the handle 11 is manufactured from polymer material via a molding or machining process. However, other materials and fabrication processes known in the art are also within the scope of this disclosure.

The shaft 12 includes a proximal portion 12a and distal portion 12b. The proximal portion 12a of the shaft 12 is coupled to the distal end 11a of the handle 11, for example, via a press-fit. In examples, not shown, the distal portion 12b of the shaft is straight, extending along the longitudinal axis L of the proximal portion 12a. In the example of FIG. 1, however, the distal portion 12b of the shaft is angled relative to a longitudinal axis L of the proximal portion 12a, which allows the surgeon to achieve the ideal insertion angle of a passing drill at a quicker rate, thereby reducing the potential of damage to cartilage and other tissue within the repair site. For the purposes of this disclosure, the shaft 12 is manufactured from metal material, such as stainless steel. However, other materials known in the art are also within the scope of this disclosure.

Turning now to FIGS. 2 and 3, the distal portion 12b of the drill guide 10 also includes at least one transverse hole 12b'. Two holes 12b' are shown in FIGS. 2 and 3, however more or fewer than two holes are contemplated by this disclosure. The holes 12b' can be used during surgery to view the anchor, specifically the orientation of the anchor, prior to inserting the anchor into bone. The holes 12b' may also be used to vent bone and other debris that may become located within the distal portion 12b of the guide 12 during surgery. In examples, a the shaft 12 may include a plurality of teeth 14 extending from the distal end 12c for facilitating maintenance of the guide 10 on the bone during surgery, thereby substantially reducing slippage of the drill guide 10 off of the bone. In other examples, the distal end 12c of the shaft 12 may have other features known in the art that would help in maintaining the drill guide 10 on the bone and reduce slippage. For the purposes of this disclosure, the holes 12b' and the teeth 14 are machined onto the shaft 12. However, other fabrication processes known in the art are contemplated by this disclosure.

Figure 4A:
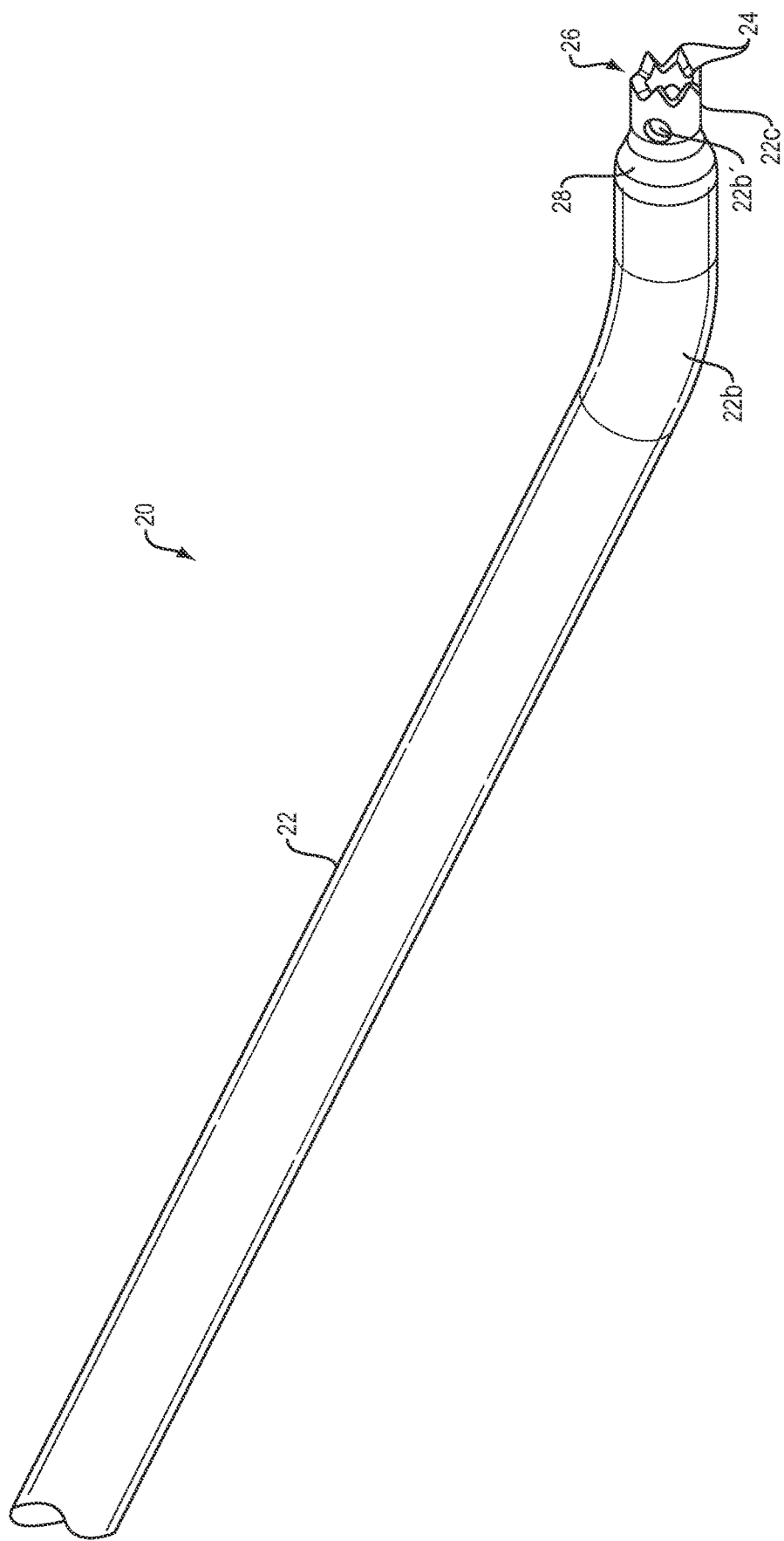
FIGS. 4A-F illustrate an example of a surgical drill guide of this disclosure.
Figure 4B:
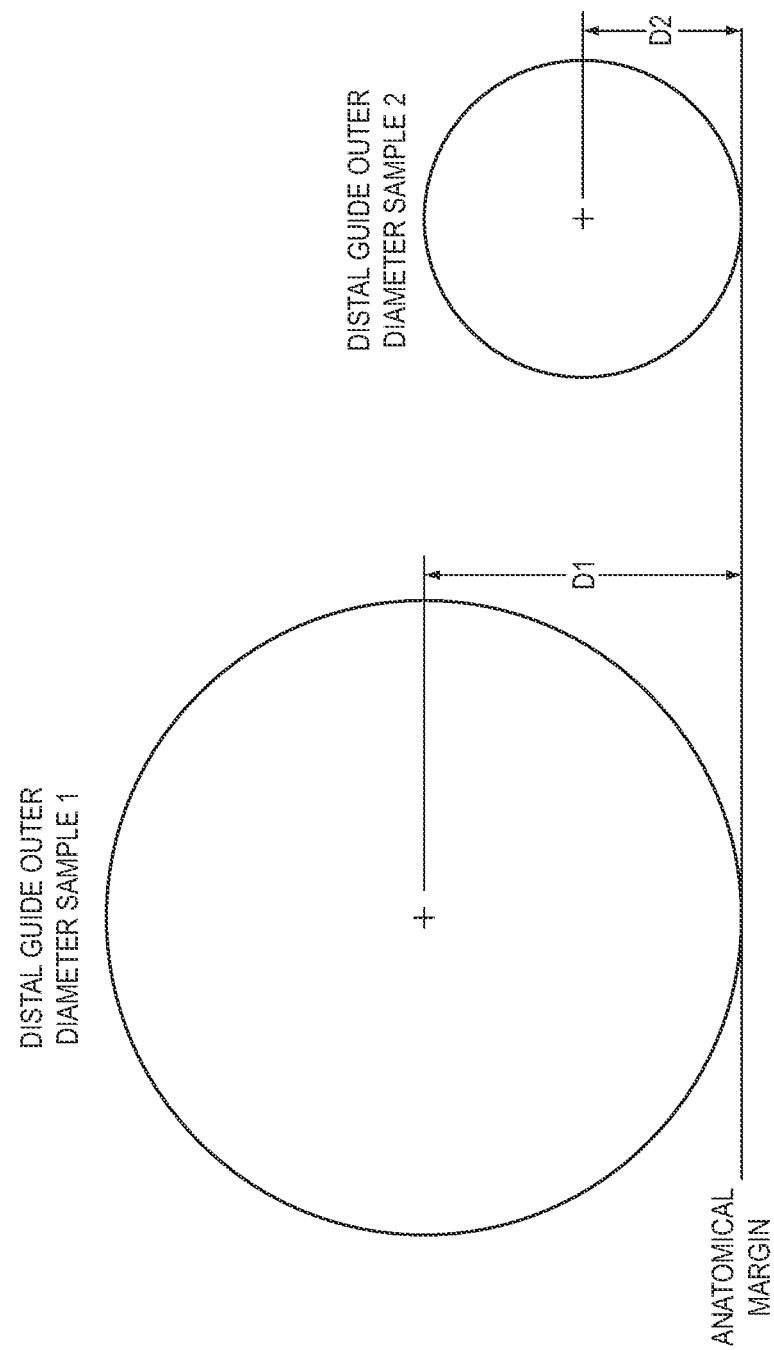

Turning now to FIG. 4A, an example of the surgical drill guide 20 of this disclosure is shown. Drill guide 20 is substantially similar to drill guide 10 except as described below. In drill guide 20, the distal end 22c is narrowed down via a tapered portion 28 relative to the remainder of the shaft 22. In examples, the tapered portion 28 can be formed in one piece (e.g., a swaging operation) or in multiple pieces that are created separately and assembled together. It is also contemplated by this disclosure that more than two distinct diameter sets could be included in the distal portion 22b. In examples (FIG. 4E), the tapered portion 28 may also comprise one or more transverse holes 22b'. The tapered portion 24 also allows for the distal end 22c to have a smaller diameter than a diameter of the shaft 22. This is advantageous in surgical procedures which require anchors to be placed as close to an anatomic margin as possible. The smaller distal end 22c allows the center point of the outer diameter to be closer to the anatomical margin, as demonstrated in FIG. 4B, and thus provide a more anatomical repair. Additionally, the smaller distal end 22c allows for less of a gap between the outer diameter of the passing instrument and the inner diameter of the distal end 22c, resulting in a more accurate trajectory. For example, if the distal end 22c had a larger inner diameter, the angle at which the passing instrument exits the distal end 22c may be larger because the passing instrument would tend to take the path of least resistance. Notably, the tapered portion 28 could also be included in straight guide shafts (not shown).

Figure 4C:
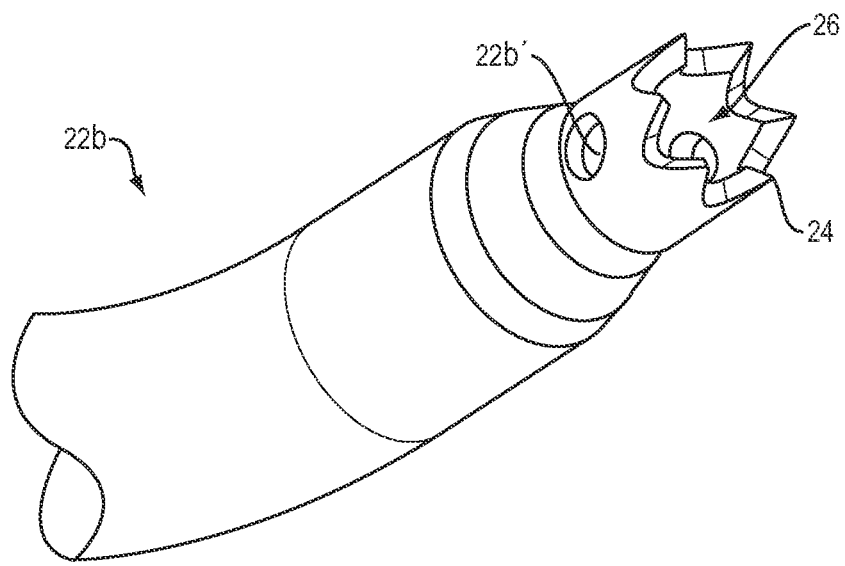
Figure 4D:
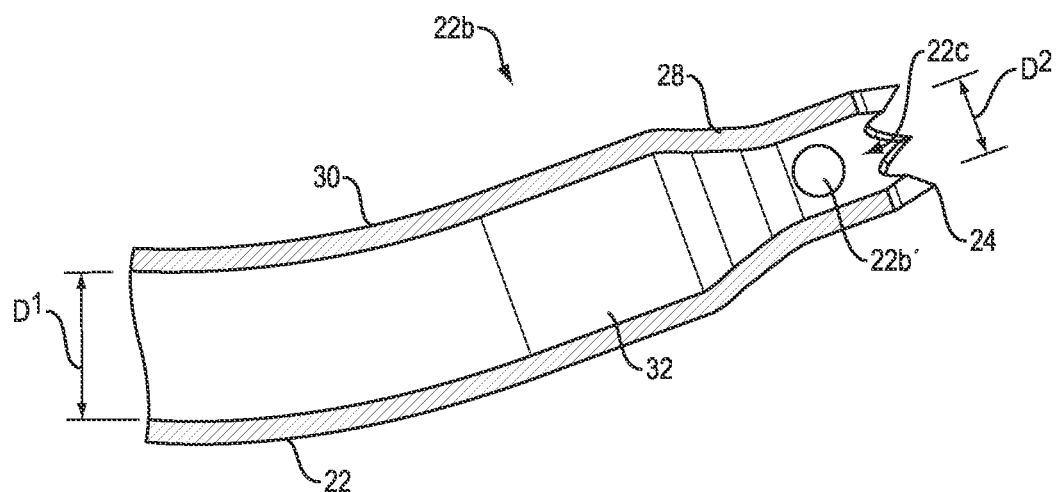
Figure 4E:
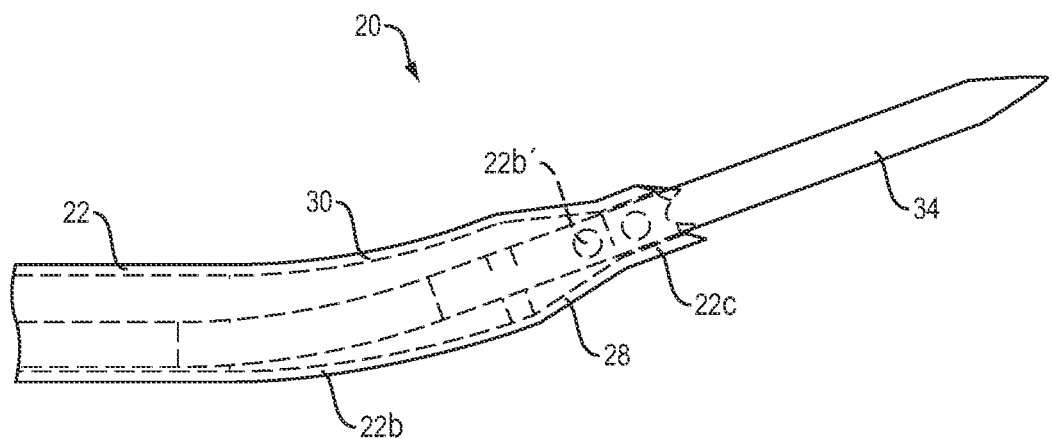

FIG. 4C is a detailed view of the distal portion 22b, including the opening 26, the holes 22b' and the plurality of teeth 24. FIG. 4D is a cross-sectional view of the distal portion 22b of FIG. 4C. As seen in FIG. 4D, the shaft 22 includes a wall 30 defining a bore 32 extending through the shaft 22. The wall 30 furthermore defines the plurality of teeth 24 extending from the distal end of the shaft 22. Notably, the selection of the diameter D1 of the bore 32 is important for achieving compatibility with passing instruments. For example, a larger diameter D1 is desirable in the shaft 22, as this allows for more room for any rigid or semi-rigid portions of the passing instruments to navigate the bend area of the shaft 22. Examples of rigid portions may include a rigid drill tip attached to a flexible drill shaft, or a rigid anchor attached to a flexible inserter. However, a smaller diameter D2 of the bore 32 is conversely desirable in the distal end 22c to tightly constrain the exit trajectory of the passing instruments, which results in predictable placement of the instruments in bone. However, it is also important that having a smaller distal end 22c does not sacrifice thickness of the wall 30 and thus the rigidity of the plurality of teeth 24. Accordingly, as shown in FIG. 4D, a thickness of the wall 30 is advantageously maintained or, as shown in FIG. 4E, increased across the tapered portion 28 from the distal portion 22b of the shaft 22 to the distal end 22c. Thus, the shaft 22 and the distal end 22c of the shaft 22 have two distinct inner and outer diameters such that the rigidity of both the shaft 22 and the teeth 24 can be maintained.

Figure 4F:
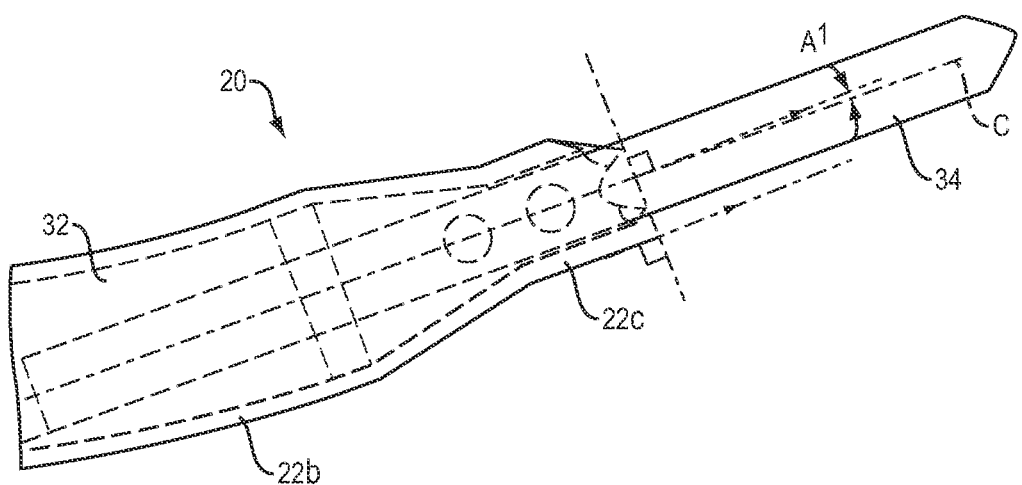

As stated above, a larger diameter of the bore in the curved region of the guide allows for a smaller bend radius and a larger bend angle of the drill guide. This configuration is favorable for hard-to-reach or hard-to-visualize anatomical areas. However, as shown in FIG. 4F, when inserted through the guide 20, passing instruments 34 tend to take the path of least resistance and cut the corner for the bent distal portion 22b of the guide 20. This results in the passing instruments 34 exiting the guide 20 at a trajectory having an angle A1 which is non-perpendicular to the distal end 22c of the guide 20 and non-parallel to the central axis C of the bore 32. As described above, a smaller diameter D2 in the distal end 22c is one method for improving the trajectory of passing instruments exiting the guide 20. For example, the larger the diameter D2 in the distal end 22c, the more misaligned the exit trajectory angle A1 will be. A reduced distal diameter D2 more closely matches the instrument trajectory to the trajectory of the guide 20. Notably, another benefit to a smaller distal diameter D2 is that it allows for minimal movement of the passing instruments as they exit the guide 20. Specifically, there is no opportunity for large variations between the trajectory of different passing instruments, such as a drill and an inserter, which could result in additional forces on the passing instruments or on an anchor during insertion due to a difference in the bone tunnel to inserter trajectory.

Figure 5:
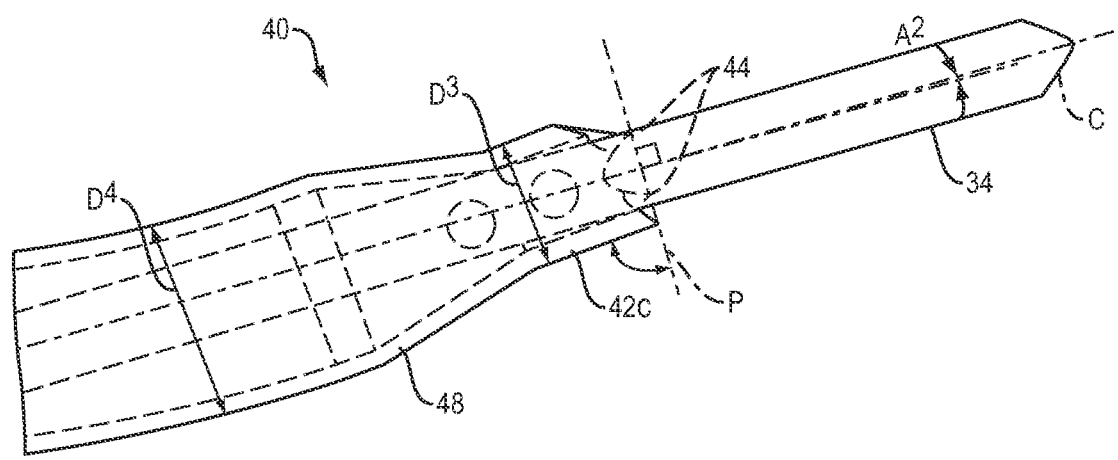
FIG. 5-6B illustrate alternative examples of the surgical drill guide of this disclosure.

FIG. 5 illustrates an alternative example of the drill guide 40 of this disclosure. Drill guide 40 is substantially similar to drill guides 10, 20 except as described below. As shown in FIG. 5, the drill guide 40 includes a proximal outer diameter D4 that is selected to be larger than a distal outer diameter D3. The distal end 42c of the drill guide 40 includes a plurality of teeth 44 for secure placement of the drill guide 40 on bone. The teeth 44 are of differing lengths such that they are angled with respect to the distal end 42c. That is, a projected plane P across the distal points of the teeth 44 is angled with respect to the outer diameter D3 of the distal end 42c such that any misalignment between the passing instruments 34 and the projected plane P of the angled teeth 44 is reduced. Thus, the passing instruments 34 exit the guide 40 at a trajectory having a reduced misalignment angle A2. Notably, this disclosure utilizes only a method of measuring trajectory with respect to a projected plane P of the angled teeth 44, and not with respect to the outer diameter D3. It is also contemplated by this disclosure that the angled teeth 44 could also be used with guides without a tapered portion 48, such as the drill guide 10 of FIG. 1. Additionally, any other drill guide system where an output trajectory of passing instruments is important may benefit from the angled teeth 44 of this disclosure. In other examples, not shown, the distal outer diameter D3 could be angled with respect to the distal inner diameter D2. This would create the same effect of allowing the passing instruments to become more aligned with the predicted trajectory of the guide 40.

As discussed above, a larger inner diameter in the curved region of the guide allows for a smaller bend radius and a larger bend angle, which is favorable for hard-to-reach or hard-to-visualize anatomical areas. However, a drill guide with a larger and more distal bend angle becomes difficult to fit through a cannula, which provides a clear access path through soft tissue into the repair site. This may result in some curved guide systems being incompatible with certain sized cannulas.

Figure 6A:
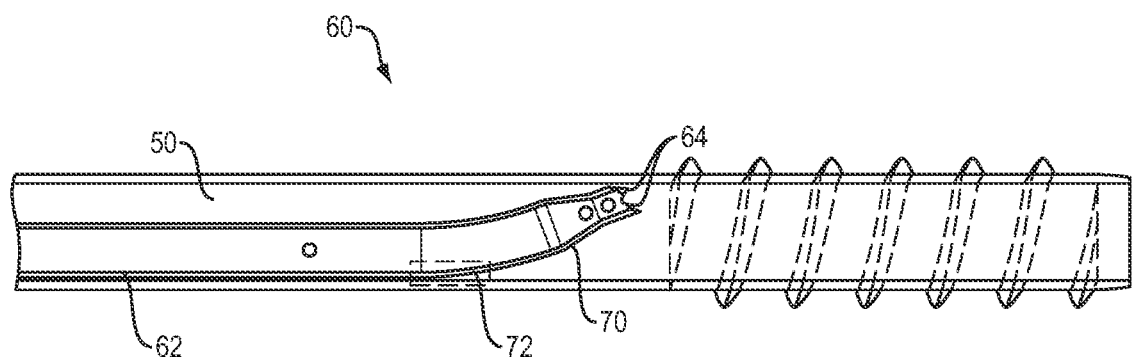
Figure 6B:
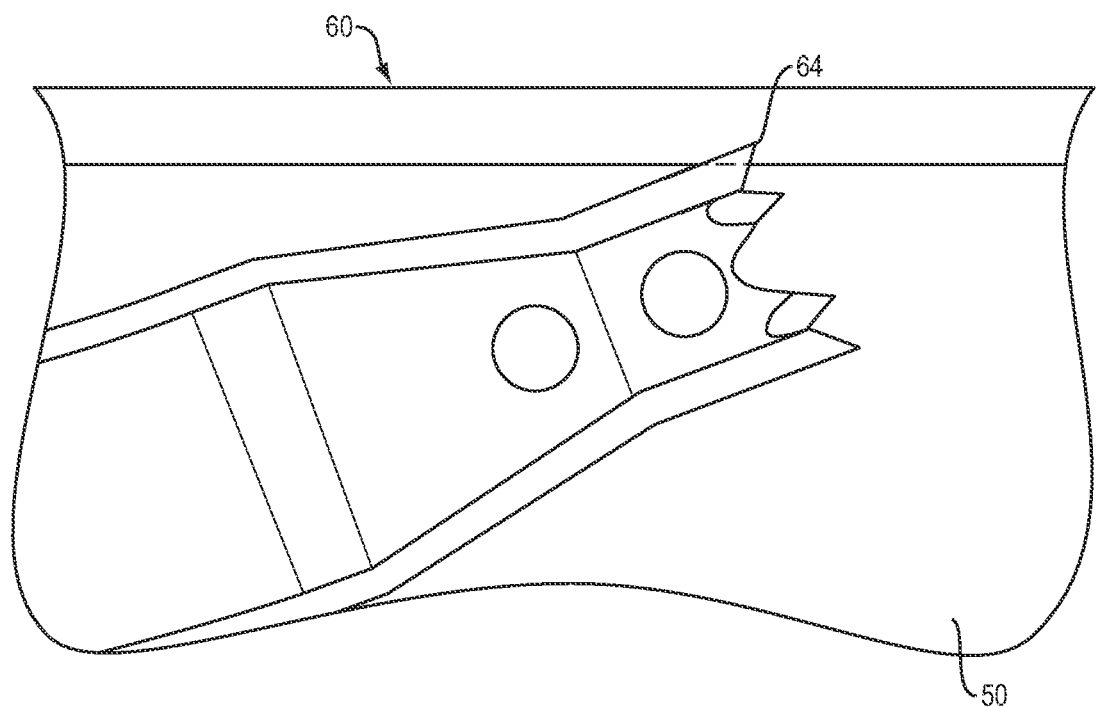

FIG. 6A illustrates an alternative example of the drill guide 60 of this disclosure. Drill guide 60 is substantially similar to drill guides 10, 20 except as described below. In drill guide 60, material from the shaft 62 of the drill guide 60 is removed at the highest point on the bend, such that the wall 70 defines a flat section 72 in the shaft 62, allowing the drill guide 60 to fit within a narrower cannula 50 than if the material had not been removed. The flat section 72 thus allows for a tighter bend radius and a more obtuse angle of the drill guide 60 without sacrificing rigidity of the shaft 62 or the teeth 64. Additionally, in examples, a top tooth 64 of the drill guide 60 is modified or removed, further facilitating the passage of the drill guide 60 through the cannula 50, as compared with a drill guide 60 having a top tooth 64 that has not been modified or removed, as shown in FIG. 6B.

As stated above, the drill guides described herein may be used for passing an instrument, such as a drill, into a repair site. A curved drill guide necessitates the use of a flexible drill to pass around the bent region of the guide. Currently, some flexible drills are made of superelastic Nitinol. Another material state of Nitinol, called martensitic Nitinol, is desirable in that it takes a permanent set when bent, which means that the forces required to push the drill around the bend are even lower than those required for superelastic Nitinol. Superelastic Nitinol is able to deform up to 8% strain and return to its original shape without permanent deformation. Martensitic Nitinol is able to reach similar strains, however it requires even less force to deform/bend than superelastic Nitinol. The low forces required to deform martensitic Nitinol make it an ideal state of Nitinol for curved guide navigation.

Examples of flexible drills of this disclosure utilize the material properties of Nitinol to control the amount of force it takes pass the Nitinol around the bend of the curved drill guide. Specifically, Nitinol can be composed of metallic states called Austenite, Martensite, and R-Phase. The metallic state of Nitinol is dependent upon certain material properties called transition temperatures. The transition temperatures available for Nitinol are austenitic start (As), austenitic finish (Af), martensitic start (Ms), martensitic finish (Mf), R-phase start (Rs), and R-phase finish (Rf). For a martensitic state of Nitinol, the operating temperature of the drill should be below the As temperature. Therefore, an As temperature above the operating temperature would ensure a more martensitic (i.e., shape memory) state of Nitinol in the drill. In a curved medical drill application, for example, the As temperature could be specified to be above both the temperature of the operating room and the body temperature of the patient. For different guide bend geometries and environmental temperatures, different transition temperatures could be specified.

One problem with martensitic Nitinol is that it is extremely flexible, which makes machining difficult. Superelastic Nitinol is more easily machined than martensitic Nitinol, since it is more rigid. Therefore, the geometry of the flexible drill can be more easily machined on Nitinol while the Nitinol is in the superelastic state. As stated above, Nitinol is capable of being heat treated to modify the transition temperatures (Af, As, Mf, Ms, Rs, Rf) to make the final product martensitic with respect to certain environmental temperatures. Therefore, one method of obtaining a martensitic drill in the final state is to machine the Nitinol in its superelastic state by setting the initial Af temperature below the operating temperature of the manufacturing environment. The drill can then be heat treated to make it martensitic after machining. Another method would be to procure the Nitinol in a martensitic state and then heat it up during machining (for example, through hot air, fluid, or changing the environmental temperature of the machining) to a temperature above the Af temperature so the Nitinol is in a superelastic state. After machining, the Nitinol of the drill would cool down back to its martensitic state for use, and therefore no heat treatment would be required, eliminating a manufacturing step.

An additional problem with Nitinol drills is that, when the drill is powered on, a martensitic Nitinol wire tends to whip around in circles at the speed of the drill, which poses a safety hazard to the user and patient. Martensitic Nitinol can also be so soft that the user loses tactile feedback from the drill during the drilling process and/or the user cannot manually maintain axial alignment of the drill within the drill guide. Accordingly, it would be advantageous to have a means of minimizing the amount of whip that occurs with martensitic Nitinol, as well as providing additional stiffness to the drill.

Figure 7:
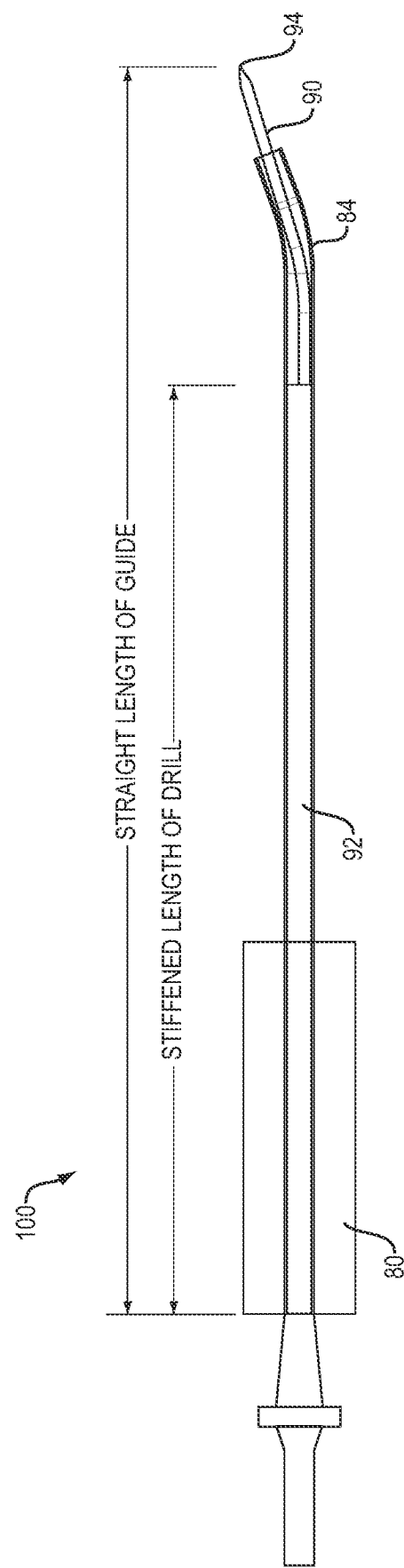
FIG. 7 illustrates a surgical drill guide system of this disclosure, including a drill guide and a flexible drill.

FIG. 7 illustrates an exemplary drill guide system 100 of this disclosure. Drill guide system 100 generally comprises a drill guide 80 and a drill 90. Drill guide 80 is substantially similar to drill guides 10, 20 except as described below. The drill 90 is comprised of martensitic Nitinol and includes a stiffening sheath 92 disposed over the part of the drill 90 that does not need to navigate the bend of the drill guide 80. Since the sheath 92 does not extend into the curved region of the drill guide 80, it does not need to be made of a bendable material, so long as the material of the sheath 92 is selected to be more rigid than the material of the drill 90. The remaining length of the drill 90 can be left unsupported. The sheath 92 advantageously minimizes the amount of whip that occurs if a user were to power the drill 90 in free air. Additionally, the sheath 92 allows compressive forces to be applied during use without the risk of buckling of the drill 90, and provides the necessary stiffness to effectively transmit those forces to the tip 94 of the drill 90. Finally, the sheath 92 allows for a tighter fit of the drill 90 to the bore 84 of the drill guide 80, allowing for the drill 90 to maintain radial alignment to the guide 80. It is further contemplated by this disclosure that the sheath 92 may be used for drills of any materials and/or geometries that require increased stiffness over some fraction of their length, for example, small diameter stainless steel wires, and for drill guides having straight guide shafts.

Another method of minimizing the amount of whip would be to change the transition temperature as described above of only the section of drill that needs to be flexible. For example, the most distal two inches of Nitinol could be in a martensitic state, whereas the rest of the drill could be superelastic. Examples of methods of making only a portion of the drill martensitic are using specialized heat treat ovens, heat treating through partial immersion in a liquid, or using heating coils capable of applying concentrated heat to a localized area.

While this disclosure has been particularly shown and described with references to preferred embodiments thereof, it will be understood by those skilled in the art that various changes in form and details may be made therein without departing from the spirit and scope of the present application as defined by the appended claims. Such variations are intended to be covered by the scope of this present application. As such, the foregoing description of examples of the present application is not intended to be limiting, the full scope rather being conveyed by the appended claims.

What is claimed is:

1. A method of surgical drilling comprising:
   introducing a surgical drill guide to a repair site, the surgical drill guide comprising:
   a shaft having a proximal portion and a distal portion, the distal portion including a tapered portion and a distal end, an outer diameter of the proximal portion selected to be larger than an outer diameter of the distal end, the proximal portion and the distal end separated by the tapered portion; and
   a bore defined by a wall of the shaft extending from a proximal end to the distal end of the shaft, the wall defining a plurality of teeth extending from the distal end;
   wherein a thickness of the wall of the distal end is selected to be the same as or greater than a thickness of the wall of the proximal portion; and
   passing a flexible drill through the bore from the proximal end to the distal end of the shaft;
   wherein the flexible drill further comprises a sheath extending through the bore from the proximal end to a region proximal to the distal portion of the shaft.

2. The method of claim 1, wherein the flexible drill comprises Nitinol.

3. The method of claim 2, wherein the Nitinol is capable of deforming up to 8% strain and returning to an original shape without permanent deformation.

4. The method of claim 1, wherein the sheath comprises a material selected to be more rigid than a material of the flexible drill.

5. The method of claim 1, wherein the distal portion of the shaft is angled relative to a longitudinal axis of the proximal portion of the shaft.

6. The method of claim 1, wherein the distal portion of the shaft includes at least one transverse hole in communication with the bore.

7. The method of claim 1, wherein the tapered portion is formed in one piece.

8. The method of claim 1, wherein the tapered portion is formed in multiple pieces.

* * * * *